United States Patent

Bankert et al.

[11] Patent Number: 5,948,419
[45] Date of Patent: Sep. 7, 1999

[54] AQUEOUS-BASED NAIL COATING COMPOSITION

[75] Inventors: Timothy J. Bankert; Karen Dumais, both of Tucson, Ariz.

[73] Assignee: The Dumais Companies, L.L.C., Tucson, Ariz.

[21] Appl. No.: 09/001,106

[22] Filed: Dec. 30, 1997

[51] Int. Cl.$^6$ .............................. A61K 6/00; A61K 7/00; A61K 7/04
[52] U.S. Cl. ............................................... 424/401; 424/61
[58] Field of Search ........................... 424/61, 401, 78.02

[56] References Cited

U.S. PATENT DOCUMENTS

| | | | |
|---|---|---|---|
| 4,158,053 | 6/1979 | Greene et al. | 424/61 |
| 5,275,645 | 1/1994 | Ternoir et al. | 106/2 |

*Primary Examiner*—Thurman K. Page
*Assistant Examiner*—Sharon Howard
*Attorney, Agent, or Firm*—Jerome M. Teplitz

[57] ABSTRACT

Aqueous-based nail coating compositions comprising an aqueous emulsion polymeric binder capable upon drying of forming a flexible hard film having adhesion to the nail, and an organofunctional hydrolyzable silane coupling agent additive in an amount effective to enhance the durability of the binder film in both its hardness and adhesion to the nail.

17 Claims, No Drawings

AQUEOUS-BASED NAIL COATING COMPOSITION

FIELD OF THE INVENTION

The present invention relates generally to aqueous-based nail coating compositions and, more particularly, to improved formulations of such compositions providing nail coatings exhibiting enhanced durability.

BACKGROUND OF THE INVENTION

The conventional nail coating compositions that have been on the market for many years are organic solvent-based lacquers employing nitrocellulose as the primary film-forming polymeric binder. It has been long recognized in the cosmetics industry that nitrocellulose lacquers fall short of being the ideal nail coating product, primarily due to the harsh organic solvents required both in the formulation of the lacquers and in the subsequent removal of the film from the nails. These organic solvents not only are flammable, malodorous and environmentally undesirable, but also may cause damage to the nails in the course of repeated usage.

In an attempt to avoid the known drawbacks associated with the organic solvent-based nitrocellulose lacquers, a great deal of effort has been expended in recent years toward developing aqueous-based nail coating compositions using in place of nitrocellulose various aqueous emulsion polymeric binders capable upon drying of forming flexible hard films having adhesion to the nail. Representative examples of the aqueous-based nail coating compositions that have previously been proposed are those described in the Greene et al U.S. Pat. No. 4,158,053, issued Jun. 12, 1979, using aqueous emulsion acrylic copolymers, and in the Koch et al U.S. Pat. No. 5,120,529, issued Jun. 9, 1992, using aqueous emulsion polyurethanes and/or polyurethane copolymers such as a polyurethane-acrylate copolymer. The major problem that has been encountered with these prior art aqueous-based formulations is in achieving commercially acceptable coating durability. The binder films formed from these formulations, when compared to nitrocellulose binder films, have been found to have significantly reduced durability in their hardness and adhesion properties, to such a degree that they either wash off or begin to peel off the nail the same day they are applied. Because of a continued lack of success in overcoming this problem, the cosmetics industry has not as yet been able to deliver the long-awaited commercially acceptable aqueous-based alternative to the conventional organic solvent-based nitrocellulose lacquers which, despite their known drawbacks, still remain by default the nail coating product of choice.

Organofunctional hydrolyzable silane coupling agents have been used for many years in various polymer applications for promoting adhesion between an organic polymer and an inorganic substrate like glass, silica, clay, talc, mica, wollastonite, asbestos and metallic surfaces. The silane coupling agents have both an organofunctional moiety selected so as to have reactivity or compatibility with the organic polymer, and hydrolyzable groups which upon hydrolysis form silanol groups having reactivity with surface hydroxyl groups on the inorganic substrate. The adhesion promoting properties of silane coupling agents have previously been used to advantage, for example, in the preparation of inorganic filler-reinforced polymer composites, the immobilization of catalytic enzymes on inorganic supports, the anchoring of polypeptides to inorganic supports in solid phase polypeptide synthesis and analysis, and the coating of ceramic and metallic surfaces with organic polymeric coatings. Use in the formulation of nail coating compositions is not among the previously known applications of silane coupling agents.

SUMMARY OF THE INVENTION

The present invention is directed to improved aqueous-based nail coating compositions utilizing silane coupling agents as additives for effectively overcoming the deficiencies in coating durability that have been associated with the aqueous-based formulations of the prior art. The aqueous-based nail coating compositions of the present invention comprise an aqueous emulsion polymeric binder capable upon drying of forming a flexible hard film having adhesion to the nail, and an organofunctional hydrolyzable silane coupling agent of the formula

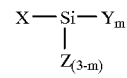

wherein X is a monovalent organofunctional moiety having reactivity or compatibility with said binder, Y is a hydrolyzable group, Z is a monovalent hydrocarbon group, and m is an integer of from 1 to 3. The silane coupling agent is present in the composition in an amount effective to enhance the durability of the binder film in both its hardness and its adhesion to the nail. This amount will generally be within the range of from about 0.01 to about 10% by weight of the coating composition.

The aqueous-based nail coating compositions of the present invention may be formulated as nail polishes, basecoats, topcoats or conditioners including the various conventional additives typically employed in these types of formulations, such as wetting agents, pigments, thickeners, antifreeze agents, drying and curing rate modifying agents, defoamers and preservatives.

DETAILED DESCRIPTION OF THE INVENTION

The aqueous-based nail coating compositions whose nail coating durability is enhanced in accordance with the present invention, have as their central component an aqueous emulsion polymeric binder which is capable upon drying of forming a film exhibiting the combined properties of flexibility, hardness and adhesion to the nail. These combined properties may be obtained with either a single binder polymer or a mixture of two or more such polymers. The polymeric binder is employed in aqueous emulsion form in which one or more binder polymers are dispersed in an aqueous phase which may contain, in addition to water, minor amounts of one or more water-miscible volatile organic solvents, such as alcohols or alcohol-ethers.

The binder polymers may be selected from a wide range of known water-dispersible polymeric materials including, for example, acrylic polymers, polyurethanes, polyurethane-acrylate copolymers, polyesters, polyamides, polyethylene, polystyrene, styrene-butadiene copolymers, styrene-acrylate copolymers, polyvinyl acetals, polyvinyl acetate, polyvinyl chloride, polyvinylidene chloride, vinyl chloride-vinyl acetate copolymers, vinyl chloride-vinylidene chloride copolymers, cellulose esters and cellulose ethers. The proper balance of flexibility and hardness will generally be achieved when the binder polymers are selected to provide the binder with a glass transition temperature ($T_g$) within the range of from about 15° C. to about 60° C., and preferably within the range of from about 30° C. to about 50° C.

A preferred class of binder polymers for use in the present invention are acrylic polymers of one or more acrylic or methacrylic acid esters of the formula

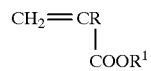

wherein R is hydrogen or methyl, and $R^1$ is $C_1$–$C_{20}$ alkyl, phenyl, benzyl, hydroxy-($C_1$–$C_4$) alkyl, $C_1$–$C_4$ alkoxy-($C_1$–$C_4$) alkyl, cyclopentyl, cyclohexyl, furyl, $C_1$–$C_4$ alkylfuryl, tetrahydrofuryl, or $C_1$–$C_4$ alkyltetrahydrofuryl. A preferred group of such acrylic and methacrylic acid esters are the alkyl acrylates and methacrylates wherein $R^1$ in the above formula is $C_1$–$C_8$ alkyl, including, for example, methyl acrylate, methyl methacrylate, ethyl acrylate, ethyl methacrylate, propyl acrylate, propyl methacrylate, isopropyl acrylate, isopropyl methacrylate, butyl acrylate, butyl methacrylate, isobutyl acrylate, isobutyl methacrylate, tertiary butyl acrylate, tertiary butyl methacrylate, pentyl acrylate, pentyl methacrylate, isopentyl acrylate, isopentyl methacrylate, neopentyl acrylate, neopentyl methacrylate, hexyl acrylate, hexyl methacrylate, isohexyl acrylate, isohexyl methacrylate, heptyl acrylate, heptyl methacrylate, isoheptyl acrylate, isoheptyl methacrylate, octyl acrylate, octyl methacrylate, isooctyl acrylate, isooctyl methacrylate, 2-ethylhexyl acrylate and 2-ethylhexyl methacrylate. A number of polymers of one or more of these alkyl acrylates and methacrylates are commercially available in aqueous emulsion form suitable for use in the present invention, for example, from Rohm and Haas Co. of Philadelphia, Pa., BASF Corp. of Parsippany, N.J., ICI Resins of Wilmington, Mass., and ICI Acrylics, KSH Inc. of St. Louis, Mo.

Binder films having the proper balance of flexibility, hardness and adhesion to the nail required in accordance with the present invention, can most advantageously be achieved by employing binders comprising a mixture of at least two of the foregoing acrylic polymers. Such mixtures will typically include at least one binder polymer having a sufficiently high $T_g$ for imparting hardness, and at least one binder polymer having a sufficiently low $T_g$ for imparting flexibility, in relative proportions so as to provide the binder polymer mixture with a $T_g$ within the range of from about 15° C. to about 60° C., and preferably within the range of from about 30° C. to about 50° C. Binder polymer mixtures that have been found to be particularly suitable are mixtures of from about 25% to about 90% by weight of a hardness-imparting homopolymer of a $C_1$–$C_2$ alkyl acrylate or methacrylate, preferably poly-(methyl methacrylate), and from about 75% to about 10% by weight of one or more flexibility-imparting copolymers of a $C_1$–$C_2$ alkyl acrylate or methacrylate, preferably methyl methacrylate, with a $C_4$–$C_8$ alkyl acrylate or methacrylate, preferably butyl acrylate or 2-ethylhexyl acrylate.

The additive employed for providing enhanced nail coating durability to the aqueous-based nail coating compositions in accordance with the present invention is an organofunctional hydrolyzable silane coupling agent of the general formula

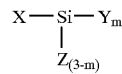

wherein X is a monovalent organofunctional moiety having reactivity or compatibility with the polymeric binder component of the composition; Y is a hydrolyzable group, such as a halogen atom, an alkoxy group, an acyloxy group or an amino group; Z is a monovalent hydrocarbon group, preferably a $C_1$–$C_{10}$ hydrocarbon group such as an alkyl group, an aryl group or an aralkyl group; and m is an integer from 1 to 3.

The silane coupling agents of the above general formula constitute a well know class of materials encompassing a large number of silane compounds which are commercially available, for example, from Gelest, Inc. of Tullytown, Pa., and PCR Incorporated of Gainesville, Fla. The organofunctional moiety of these silane coupling agents, represented by X in the above formula, typically contains at least one functional group selected from acrylyl, methacrylyl, epoxy, amino, ureido, isocyanato, thiocyanato, mercapto, styryl, phenyl, haloalkylphenyl, vinyl and alkyl.

Representative examples of these commercially available silane coupling agents suitable for use in the present invention are 3-acryloxypropyltrimethoxysilane, 3-methacryloxypropyltimethoxysilane, 3-methacryloxypropyltris(methoxyethoxy)silane, 3-glycidoxypropyltrimethoxysilane, (3-glycidoxypropyl) methyldiethoxysilane, 2-(3,4-epoxycyclohexyl) ethyltrimethoxysilane, 3-aminopropyltriethoxysilane, (3-aminopropyl)methyldiethoxysilane, N-(2-aminoethyl)-3-aminopropyltrimethoxysilane, N-(2-aminoethyl)-3-aminopropylmethyldimethoxysilane, (aminoethylaminomethyl)phenethyltrimethoxysilane, 3-(1-aminopropoxy)-3,3-dimethyl-1-propenyltrimethoxysilane, N-phenylaminopropyltrimethoxysilane, (3-trimethoxysilylpropyl)diethylenetriamine, ureidopropyltriethoxysilane, 3-isocyanatopropyltriethoxysilane, 3-thiocyanatopropyltriethoxysilane, 3-mercaptopropyltriethoxysilane, 3-(N-styrylmethyl-2-aminoethylamino)propyltrimethoxysilane hydrochloride, phenyltriethoxysilane, phenethyltrimethoxysilane, (p-chloromethyl)phenyltrimethoxysilane, (chloromethyl) phenylethyltrimethoxysilane, vinyltrimethoxysilane, vinyltriethoxysilane, and allyltrimethoxysilane.

As will be apparent from the definition of X in the above silane coupling agent general formula, the selection of an appropriate silane coupling agent additive for use in any given aqueous-based nail coating composition in accordance with the present invention, will be based upon the particular polymeric binder component employed in the composition so as to satisfy the requirement that the organofunctional moiety of the silane coupling agent have reactivity or compatibility with such polymeric binder component. For most of the binder polymers contemplated for use in the present invention, and particularly with the preferred embodiments of the invention employing acrylic polymers as the binder polymers, the preferred organofunctional moieties for satisfying this requirement contain at least one functional group selected from acrylyl, methacrylyl, epoxy, amino and ureido. Specific organofunctional moieties containing such functional groups include, for example, 3-acryloxypropyl, 3-methacryloxypropyl, 3-glycidoxypropyl, 2-(3,4-epoxycyclohexyl)ethyl, 3-aminopropyl, N-(2-aminoethyl)-3-aminopropyl, (aminoethylaminomethyl)phenethyl, 3-(1-aminopropoxy)-3,3-dimethyl-1-propenyl, N-phenylaminopropyl, diethylenetriaminopropyl, and 3-ureidopropyl.

The organofunctional moieties containing amino functional groups are particularly versatile in having reactivity or compatibility with a wide range of different polymer types suitable for use as binder polymers in accordance with the present invention. This would include, for example, acrylic polymers, polyurethanes, polyesters, polyamides, polyethylene and polyvinyl polymers.

The preferred silane coupling agent additives for use in the present invention are trialkoxysilanes of the above general formula, wherein X is a monovalent organofunctional moiety containing at least one functional group selected from acrylyl, methacrylyl, epoxy, amino and ureido; Y is a hydrolyzable alkoxy group, e.g., methoxy, ethoxy, or methoxyethoxy, and m is 3. A representative example of a silane coupling agent additive within the preferred group is 3-methacryloxypropyltrimethoxysilane, which has been found to be particularly suitable for use in preferred embodiments of the invention employing binder polymer mixtures of alkyl acrylate and/or methacrylate polymers.

The aqueous-based nail coating compositions of the present invention are formulated by adding the silane coupling agent additive to an aqueous emulsion of the polymeric binder component. Where the polymeric binder component comprises two or more binder polymers, the aqueous emulsion may suitably be a blend of separate aqueous emulsions of each binder polymer. Such aqueous emulsions may be prepared by aqueous emulsion polymerization of the monomeric precursors of the binder polymers in accordance with polymerization techniques well known in the art, or alternatively may be commercially available aqueous emulsion forms of the polymers. Many of the binder polymers suitable for use in formulating the nail coating compositions of the present invention, including the preferred group of alkyl acrylate and methacrylate acrylic polymers, such as poly-(methyl methacrylate), methyl methacrylate-butyl acrylate copolymers and methyl methacrylate-2-ethylhexyl acrylate copolymers, are commercially available in aqueous emulsion form.

The polymeric binder component will generally be present in the nail coating composition in an amount ranging from about 30 to about 55%, preferably from about 35 to about 45%, by weight of the composition. The silane coupling agent additive is present in the composition in an amount effective to enhance the durability of the polymeric binder film in both its hardness and its adhesion to the nail. This amount will generally be within the range of from about 0.01 to about 10%, preferably from about 0.1 to about 5%, by weight of the composition.

In accordance with the present invention, the aqueous emulsion polymeric binder and the silane coupling agent additive are used as the basic ingredients in formulating various types of aqueous-based nail coating compositions exhibiting enhanced nail coating durability, including nail polishes, basecoats, topcoats and conditioners. In addition to these basic ingredients, such nail coating formulations will generally contain various conventional additives typically employed in these types of formulations, such as wetting agents, pigments, thickeners, antifreeze agents, drying and curing rate modifying agents, defoamers and preservatives. The requirements for any one or more of these additives will vary depending upon the particular type of nail coating composition being formulated.

Wetting agents are conventionally added to nail coating compositions for the dual purpose of improving the flow characteristics of the coating composition so that it can be uniformly applied to the nail, and imparting water repellency to the dried nail coating film. Examples of conventional wetting agent additives are hydrolyzable silanes, polyalkyl ethers, sulfonated oils, alkyl sulfonates and benzoic naphthenic acids. The preferred wetting agent additives for use in the aqueous-based nail coating compositions of the present invention are the hydrolyzable silanes due to their compatibility with the silane coupling agent additives. These hydrolyzable silane wetting agents are generally represented by the formula $R^2_{(4-n)}$—Si—$R^3_n$, wherein $R^2$ is a monovalent hydrocarbon group, preferably a $C_1$–$C_{10}$ hydrocarbon group such as an alkyl group, an aryl group or an aralkyl group; $R^3$ is a hydrolyzable group, such as a halogen atom, an alkoxy group, an acyloxy group or an amino group; and n is an integer of from 1 to 4. Representative examples of hydrolyzable silane wetting agent additives suitable for use in the nail coating compositions of the present invention include tetraethoxysilane, methyltrichlorosilane, methyltrimethoxysilane, methyltriethoxysilane, dimethyldichlorosilane, dimethyldimethoxysilane, dimethyldiethoxysilane, trimethylchlorosilane, trimethylmethoxysilane and trimethylethoxysilane. The wetting agent additive will generally be present in the nail coating composition in an amount within the range of from about 0.03 to about 15%, preferably from about 0.5 to about 7%, by weight of the composition.

A water-dispersible pigment additive will generally be included in the nail polish formulations of the present invention. The pigment additive may be selected from a wide number of FDA-certified organic and inorganic pigments well known to those skilled in the cosmetics art. Examples of such pigments include D&C Red No. 6 Barium Lake, D&C Red No. 7 Calcium Lake, D&C Red No. 34 Calcium Lake, D&C Yellow No. 5 Aluminum or Zirconium Lake, D&C Yellow No. 6 Aluminum Lake, titanium dioxide, brown iron oxide, black iron oxide, red iron oxide, chrome oxide, guanine, bismuth oxychloride, and titanium dioxide coated mica. The tendency of the pigment to settle and migrate within the nail polish composition has been found to be greatly reduced when the pigment is employed in hydrophobic form obtained by precoating the pigment with an organopolysiloxane in accordance with the Socci et al U.S. Pat. No. 4,832,944 issued May 23, 1989, the disclosure of which is incorporated herein by reference. The pigment additive is generally incorporated into the nail polish formulation as a color concentrate formed as an aqueous suspension of the pigment containing one or more suspending agents, such as mineral oil, talc methicone or dimethicone. The pigment content of the nail polish formulation will generally be within the range of from about 0.3 to about 20%, preferably from about 0.3 to about 10%, by weight of the composition.

Thickening agents are conventionally added to nail coating compositions for the purpose of increasing viscosity and stabilizing the pigments in suspension. Suitable thickening agent additives for use in the nail coating compositions of the present invention include, for example, various clays such as bentonite, montmorillonite, hectorite and smectite; and various synthetic polymers such as polyacrylates and polyurethanes. The thickening agent additive will generally be present in the nail polish, basecoat and topcoat formulations of the present invention in an amount within the range of from about 0.02 to about 12%, preferably from about 0.1 to about 5%, by weight of the composition.

In order to prevent the development of crinkling effects when the nail coating composition of the present invention is applied at temperatures significantly below normal room temperature, it has been found desirable to include in the composition an antifreeze agent additive, such as propylene glycol, glycerin or 1,3-butylene glycol. The antifreeze agent additive will generally be present in the nail coating composition in an amount within the range of from about 0.1 to about 25%, preferably from about 1 to about 12%, by weight of the composition.

Drying and curing rate modifying agents are conventionally added to nail coating compositions for the purpose of controlling both the drying time and cure time of the applied film so that these processes occur in as short a period as possible without the development of crinkling effects in the film. Ideally, the film should dry to the touch within 45 to 90 seconds following application, and should cure in less than an hour to a hardness sufficient to withstand normal tasks without fear of chipping. Various drying and curing rate accelerators and retarders can be used, either singly or in combination, for controlling the drying and cure times to within these ranges. Examples of suitable drying and curing rate modifying agents include polymeric materials such as polysaccharide resin and polyether-modified dimethylpolysiloxane, and solvents such as methyl ethyl ketone, 1,1,1-trichloroethane, ethylene glycol monobutyl ether, diethylene glycol monomethyl ether, propylene glycol monomethyl ether, dipropylene glycol monomethyl ether, 2,2,4-trimethyl-1,3-pentanediol monoisobutyrate, trimethylene glycol, diethylene glycol, propylene glycol, and the like. As a general rule, lower boiling point solvents will accrates,e the drying and curing rates, while higher boiling point solvents will retard them. The drying and curing rate modifying agent additive will generally be present in the nail polish, basecoat and topcoat formulations of the present invention in an amount within the range of from about 0.01 to about 15%, preferably from about 0.1 to about 8%, by weight of the composition.

Other conventional additives commonly employed in nail coating formulations include defoamers for preventing foam and bubbles during manufacturing and application to the nail, such as polysiloxanes and polyoxyethylene-polyoxypropylene condensates; and preservatives to prevent bacterial and fungal growth during storage, such as ($C_1$–$C_6$ alkyl)-p-hydroxybenzoic acid esters and potassium sorbate.

Representative nail polish formulations in accordance with the present invention are illustrated in the following Examples 1–9, in which all percentages listed are by weight.

| Ingredient | Percent |
| --- | --- |
| Example 1 | |
| Poly-(methyl methacrylate) | 28 |
| Copolymer of methyl methacrylate and 2-ethylhexyl acrylate | 2 |
| Copolymer of methyl methacrylate and butyl acrylate | 7 |
| 3-Methacryloxypropyltrimethoxysilane | 1 |
| Tetraethoxysilane | 1 |
| Propylene glycol | 5 |
| Pigment | 5 |
| Polyacrylate thickening agent | 1 |
| Methyl ethyl ketone | 1 |
| Water and diluents | 49 |
| | 100 |
| Example 2 | |
| Poly-(methyl methacrylate) | 27 |
| Copolymer of methyl methacrylate and 2-ethylhexyl acrylate | 5 |
| Copolymer of methyl methacrylate and butyl acrylate | 4 |
| 3-Methacryloxypropyltrimethoxysilane | 2 |
| Tetraethoxysilane | 1 |
| Propylene glycol | 6 |
| Pigment | 4 |
| Polyacrylate thickening agent | 3 |
| Methyl ethyl ketone | 3 |
| Water and diluents | 45 |
| | 100 |
| Example 3 | |
| Poly-(methyl methacrylate) | 26 |
| Copolymer of methyl methacrylate and 2-ethylhexyl acrylate | 4 |
| Copolymer of methyl methacrylate and butyl acrylate | 6 |
| 3-Methacryloxypropyltrimethoxysilane | 2 |
| Tetraethoxysilane | 1 |
| Propylene glycol | 5 |
| Pigment | 6 |
| Polyacrylate thickening agent | 2 |
| Methyl ethyl ketone | 2 |
| Water and diluents | 46 |
| | 100 |
| Example 4 | |
| Poly-(methyl methacrylate) | 24 |
| Copolymer of methyl methacrylate and 2-ethylhexyl acrylate | 6 |
| Copolymer of methyl methacrylate and butyl acrylate | 5 |
| 3-Methacryloxypropyltrimethoxysilane | 2 |
| Tetraethoxysilane | 1 |
| Propylene glycol | 6 |
| Pigment | 5 |
| Polyacrylate thickening agent | 3 |
| Methyl ethyl ketone | 3 |
| Water and diluents | 45 |
| | 100 |
| Example 5 | |
| Poly-(methyl methacrylate) | 21 |
| Copolymer of methyl methacrylate and 2-ethylhexyl acrylate | 7 |
| Copolymer of methyl methacrylate and butyl acrylate | 7 |
| 3-Methacryloxypropyltrimethoxysilane | 3 |
| Tetraethoxysilane | 2 |
| Propylene glycol | 6 |
| Pigment | 4 |
| Polyacrylate thickening agent | 3 |
| Methyl ethyl ketone | 2 |
| Water and diluents | 45 |
| | 100 |
| Example 6 | |
| Poly-(methyl methacrylate) | 18 |
| Copolymer of methyl methacrylate and 2-ethylhexyl acrylate | 7 |
| Copolymer of methyl methacrylate and butyl acrylate | 17 |
| 3-Methacryloxypropyltrimethoxysilane | 1 |
| Tetraethoxysilane | 1 |
| Propylene glycol | 3 |
| Pigment | 0.4 |
| Polysaccharide resin | 0.2 |
| Water and diluents | 52.4 |
| | 100.0 |
| Example 7 | |
| Poly-(methyl methacrylate) | 16 |
| Copolymer of methyl methacrylate and 2-ethylhexyl acrylate | 13 |
| Copolymer of methyl methacrylate and butyl acrylate | 13 |
| 3-Methacryloxypropyltrimethoxysilane | 1 |
| Tetraethoxysilane | 2 |

-continued

| Ingredient | Percent |
|---|---|
| Propylene glycol | 2 |
| Pigment | 0.9 |
| Polysaccharide resin | 1 |
| Water and diluents | 51.1 |
| | 100.0 |

Example 8

| Poly-(methyl methacrylate) | 13 |
|---|---|
| Copolymer of methyl methacrylate and 2-ethylhexyl acrylate | 10 |
| Copolymer of methyl methacrylate and butyl acrylate | 18 |
| 3-Methacryloxypropyltrimethoxysilane | 2 |
| Tetraethoxysilane | 1 |
| Propylene glycol | 2 |
| Pigment | 1.8 |
| Polysaccharide resin | 1.3 |
| Water and diluents | 50.9 |
| | 100.0 |

Example 9

| Poly-(methyl methacrylate) | 11 |
|---|---|
| Copolymer of methyl methacrylate and 2-ethylhexyl acrylate | 12 |
| Copolymer of methyl methacrylate and butyl acrylate | 17 |
| 3-Methacryloxypropyltrimethoxysilane | 2 |
| Tetraethoxysilane | 2 |
| Propylene glycol | 4 |
| Pigment | 1.2 |
| Polysaccharide resin | 2 |
| Water and diluents | 48.8 |
| | 100.0 |

Example 10
A representative basecoat formulation in accordance with the present invention is illustrated below.

| Poly-(methyl methacrylate) | 24 |
|---|---|
| Copolymer of methyl methacrylate and 2-ethylhexyl acrylate | 12 |
| Copolymer of methyl methacrylate and butyl acrylate | 6 |
| 3-Methacryloxypropyltrimethoxysilane | 2 |
| Propylene glycol | 4 |
| Water and diluents | 52 |
| | 100 |

Example 11
A representative topcoat formulation in accordance with the present invention is illustrated below.

| Poly-(methyl methacrylate) | 21 |
|---|---|
| Copolymer of methyl methacrylate and 2-ethylhexyl acrylate | 7 |
| Copolymer of methyl methacrylate and butyl acrylate | 14 |
| 3-Methacryloxypropyltrimethoxysilane | 2 |
| Propylene glycol | 4 |
| Water and diluents | 52 |
| | 100 |

What is claimed is:

1. In an aqueous-based nail coating composition comprising an aqueous emulsion polymeric binder capable upon drying of forming a flexible hard film having adhesion to the nail, the improvement wherein said aqueous-based nail coating composition includes an organofunctional hydrolyzable silane coupling agent of the formula

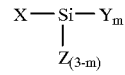

wherein X is a monovalent organofunctional moiety having reactivity or compatibility with said aqueous emulsion polymeric binder, Y is a hydrolyzable group, Z is a monovalent hydrocarbon group, and m is an integer of from 1 to 3, said organofunctional hydrolyzable silane coupling agent being present in said aqueous-based nail coating composition in an amount effective to enhance the durability of the binder film in both its hardness and its adhesion to the nail.

2. The nail coating composition of claim 1, wherein said organofunctional hydrolyzable silane coupling agent is present in said aqueous-based nail coating composition in an amount within the range of from about 0.01 to about 10% by weight of the composition.

3. The nail coating composition of claim 1, wherein Y is selected from the group consisting of a halogen atom, an alkoxy group, an acyloxy group and an amino group; and Z is a $C_1$–$C_{10}$ hydrocarbon group selected from the group consisting of an alkyl group, an aryl group and an aralkyl group.

4. The nail coating composition of claim 3, wherein X contains at least one functional group selected from the group consisting of acrylyl, methacrylyl, epoxy, amino, ureido, isocyanato, thiocyanato, mercapto, styryl, phenyl, haloalkylphenyl, vinyl and allyl.

5. The nail coating composition of claim 1, wherein said aqueous emulsion polymeric binder has a glass transition temperature within the range of from about 15° C. to about 60° C.

6. The nail coating composition of claim 5, wherein said aqueous emulsion polymeric binder has a glass transition temperature within the range of from about 30° C. to about 50° C.

7. The nail coating composition of claim 5, wherein said aqueous emulsion polymeric binder comprises an acrylic polymer of one or more acrylic or methacrylic acid esters of the formula

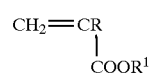

wherein R is hydrogen or methyl, and $R^1$ is $C_1$–$C_{20}$ alkyl, phenyl, benzyl, hydroxy-($C_1$–$C_4$) alkyl, $C_1$–$C_4$ alkoxy-($C_1$–$C_4$) alkyl, cyclopentyl, cyclohexyl, furyl, $C_1$–$C_4$ alkylfuryl, tetrahydrofuryl, or $C_1$–$C_4$ alkyltetrahydrofuryl.

8. The nail coating composition of claim 7, wherein $R^1$ is $C_1$–$C_8$ alkyl.

9. The nail coating composition of claim 7, wherein said aqueous emulsion polymeric binder comprises a mixture of at least two of said acrylic polymers.

10. The nail coating composition of claim 9, wherein said aqueous emulsion polymeric binder comprises a mixture of a homopolymer of a $C_1$–$C_2$ alkyl acrylate or methacrylate and one or more copolymers of a $C_1$–$C_2$ alkyl acrylate or methacrylate with a $C_4$–$C_8$ alkyl acrylate or methacrylate.

11. The nail coating composition of claim 10, wherein said aqueous emulsion polymeric binder comprises a mixture of poly-(methyl methacrylate) and one or more copolymers of methyl methacrylate with an alkyl acrylate selected from the group consisting of butyl acrylate and 2-ethylhexyl acrylate.

12. The nail coating composition of claim 7, wherein X contains at least one functional group selected from the group consisting of acrylyl, methacrylyl, epoxy, amino and ureido.

13. The nail coating composition of claim 12, wherein X is selected from the group consisting of 3-acryloxypropyl, 3-methacryloxypropyl, 3-glycidoxypropyl, 2-(3,4-epoxycyclohexyl)ethyl, 3-aminopropyl, N-(2-aminoethyl)-3-aminopropyl, (aminoethylaminomethyl)phenethyl, 3-(1-aminopropoxy)-3,3-dimethyl-1-propenyl, N-phenylaminopropyl, diethylenetriaminopropyl, and 3-ureidopropyl.

14. The nail coating composition of claim 1, wherein said aqueous-based nail coating composition further includes a hydrolyzable silane wetting agent of the formula $R^2_{(4-n)}$—Si—$R^3_n$, wherein $R^2$ is a monovalent hydrocarbon group, $R^3$ is a hydrolyzable group, and n is an integer of from 1 to 4.

15. The nail coating composition of claim 14, wherein said aqueous emulsion polymeric binder comprises a mixture of poly-(methyl methacrylate) and one or more copolymers of methyl methacrylate with an alkyl acrylate selected from the group consisting of butyl acrylate and 2-ethyl hexyl acrylate.

16. The nail coating composition of claim 15, wherein said organofunctional hydrolyzable silane coupling agent is 3-methacryloxypropyltrimethoxysilane and said hydrolyzable silane wetting agent is tetraethoxysilane.

17. The nail coating composition of claim 1, wherein said aqueous-based nail coating composition further includes a pigment.

* * * * *